United States Patent [19]

Israel et al.

[11] Patent Number: 4,610,977
[45] Date of Patent: Sep. 9, 1986

[54] N-ALKYL AND N-BENZYL ADRIAMYCIN DERIVATIVES

[75] Inventors: Mervyn Israel; Ramakrishnan Seshadri, both of Germantown, Tenn.

[73] Assignee: The University of Tennessee Research Corporation, Knoxville, Tenn.

[21] Appl. No.: 720,697

[22] Filed: Apr. 8, 1985

[51] Int. Cl.$^4$ .................... A61K 31/71; C07H 15/24
[52] U.S. Cl. ......................................... 514/34; 536/6.4
[58] Field of Search ......................... 536/6.4; 514/34

[56] References Cited

U.S. PATENT DOCUMENTS

| | | | |
|---|---|---|---|
| 3,590,028 | 6/1971 | Arcamone et al. | 536/6.4 |
| 3,803,124 | 4/1974 | Arcamone et al. | 536/6.4 |
| 4,035,566 | 7/1977 | Israel et al. | 536/6.4 |
| 4,177,264 | 12/1979 | Wu et al. | 536/6.4 |
| 4,250,303 | 2/1981 | Wu et al. | 536/6.4 |
| 4,299,822 | 11/1981 | Israel et al. | 536/6.4 |

FOREIGN PATENT DOCUMENTS 1368680 12/1972 United Kingdom .

OTHER PUBLICATIONS

Arcamone et al., *Journal of Medical Chemistry*, 1974, vol. 17, No. 3, pp. 335–337.
Tong et al., *J. Med. Chem.*, vol. 22, 912–918, (1979).

*Primary Examiner*—Johnnie R. Brown
*Assistant Examiner*—Elli Peselel

[57] ABSTRACT

Compounds having the structure

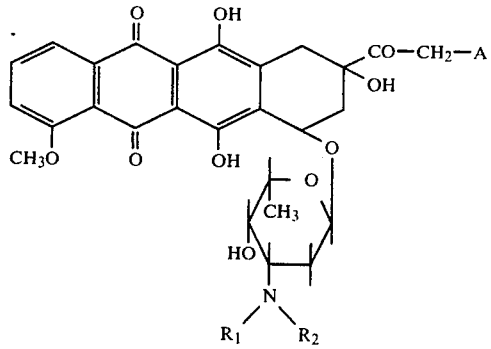

in which A is alkanoate having from 4 to 10 carbon atoms, hemiadipate, or hemiglutarate, and $R_1$ and $R_2$ are n-propyl, or n-butyl, or $R_1$ is hydrogen, n-propyl or n-butyl and $R_2$ is benzyl, and their corresponding non-toxic pharmacologically acceptable acid salts. The compounds are useful as active agents in therapeutic compositions having antitumor activity.

10 Claims, No Drawings

N-ALKYL AND N-BENZYL ADRIAMYCIN DERIVATIVES

This invention was made during the course of work supported by research grant awards from the National Cancer Institute, Department of Health and Human Services, and the Government has certain rights in the invention.

The invention described herein relates to novel chemical compounds having extraordinarily high antitumor activity against murine P388 or L1210 leukemias in standard assay systems as compared to related compounds, together with low toxicity; it also relates to therapeutic compositions containing these compounds together with a pharmacologically acceptable non-toxic carrier which are useful inter alia for administration to mammals, such as mice, having certain tumors, for extending their life spans.

Adriamycin and daunomycin (the former differs from the latter in having a hydroxyl group in the 14-position) and related compounds have been described in U.S. Pat. Nos. 3,590,028 and 3,803,124. Adriamycin carboxylated in the 14-position has been described in British Pat. No. 1,368,680. N-trifluoroacetyladriamycin carboxylated in the 14-position has been described in U.S. Pat. Nos. 4,035,566 and 4,299,822; and N-alkyl and N-benzyl adriamycin have been described in Tong et al., J. Med. Chem., Vol. 22, 912-918 (1979). See also Wu et al. U.S. Pat. No. 4,177,264 (1979).

It has now been found that certain N-substituted 14-carboxylated adriamycin compounds display greatly enhanced antitumor activity as compared to other adriamycin derivatives, as well as low toxicity. Adriamycin and daunomycin have both been found to possess antitumor activity and have been found to be effective clinically against certain malignant tumors: for example, for the induction of remission in acute leukemia; and adriamycin has shown clinical efficacy against certain solid tumors. They are among the most important agents used in chemotherapy of neoplastic disease. However, chemotherapy with adriamycin or daunomycin is accompanied by a variety of toxicities which limit the effectiveness of the compounds or of therapeutic compositions containing them as active agents, particularly limiting their long-term use. The compounds of the present invention are those having the following composition

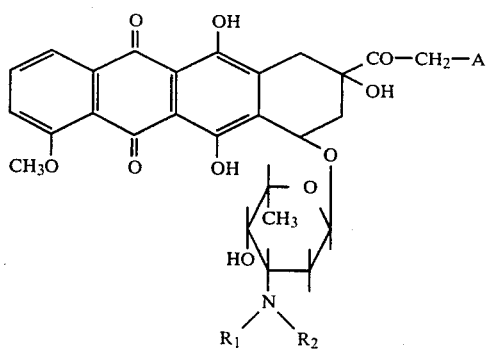

in which A is alkanoate having from 4 to 10 carbon atoms, or in which A is hemiadipate, or hemiglutarate, and in which $R_1$ and $R_2$ are n-propyl or n-butyl, or in which $R_1$ is hydrogen, n-propyl or n-butyl and $R_2$ is benzyl, and their corresponding non-toxic pharmacologically acceptable acid salts. Among suitable alkanoates are butanoate, isobutyrate, pentanoate, valerate, hexanoate, caproate, octanoate, caprylate, decanoate, and caprate. In the preferred compounds, A is valerate.

The novel compounds of the invention can be made from adriamycin by first preparing adriamycin 14-alkanoate or O-hemiadipate or O-hemiglutarate, using the acylation procedures described in Israel et al., U.S. Pat. Nos. 4,035,566 and 4,299,822 or in British Pat. No. 1,368,680, followed by reductive amination by reacting with the appropriate aldehyde in the presence of cyanoborohydride, the same general procedure as described by Tong et al., J. Med. Chem., Vol. 22, 912-918 (1979). In another procedure the carboxylated adriamycin can be directly alkylated or benzylated by reaction with the appropriate halide in the presence of an acid acceptor. The latter procedure is preferred, particularly when the halide is iodide, because of its simplicity, ease of control, and elimination of reducing agent. Mono- versus di-substitution can be controlled by the amount of halide reagent and the time period of the reaction. The reaction can conveniently be carried out at room temperature but higher temperatures up to 50° C. or even higher can be used if desired. Any suitable solvent can be used such as dimethylformamide, dimethylsulfoxide, isopropyl alcohol, or the like, of which dimethylformamide is preferred. The direct alkylation procedure also allows for the facile introduction of two different substituents on the glycoside nitrogen by sequential reactions with different alkyl or benzyl halides, for example N,N-n-propylbenzyl or N,N-n-propyl-n-butyl substituents.

The therapeutic compositions of the present invention containing the novel compounds of the present invention as the active agents can be prepared by dispersing or dissolving the active agent in any pharmaceutically or pharmacologically acceptable non-toxic carrier suitable for the desired mode of administration, which may be parenteral, that is, by injection which is intravenous, intramuscular, intraperitoneal, or other conventional mode. Suitable carriers include an aqueous medium containing nonionic emulsifying agents such as polyethoxylated castor oil, polyethoxylated sorbitan monooleate, or the like, which can be present in amounts up to 10% by weight, as well as ethanol, to enhance the solubility of the novel compounds where necessary. There may also be used as carriers such organic liquids as dimethyl sulfoxide, propylene glycol, glycerol, peanut oil, sesame oil, or the like. For the adipate or glutarate products, an aqueous medium buffered to the physiologic range, pH 7.2-7.5 with any suitable buffer such as tris, phosphates, or bicarbonates, can be used.

The following examples are intended to illustrate more fully the nature of the present invention without acting as a limitation upon its scope.

EXAMPLE 1

N-Benzyladriamycin-14-valerate

Method A

Adriamycin-14-valerate HCl (300 mg, 0.45 mmol) was stirred in acetonitrile water (3:1, 15 ml) and benzaldehyde (0.93 ml) for 30 min. NaCNBH₃ (50 mg) was added and stirring was continued for 30 min. longer at room temperature. The mixture was diluted with water (10 ml) and extracted with CHCl₃ (2×50 ml). The CHCl₃ extract was dried over sodium sulfate, the solvent evaporated, and the residue was chromatographed on silica gel (20 g). CHCl$_3$—MeOH (0.5%) eluted pure N-benzyladriamycin-14-valerate (150 mg, 44%); the hydrochloride salt was homogeneous on tlc (CHCl$_3$—MeOH, 9:1, R$_f$ 0.52) and hplc (phenylsilylether column, CH$_3$CN—pH 4.0 ammonium formate buffer, gradient elution, 35% to 65% CH$_3$CN over 6 min., r.t.=7.90 min.); uv-vis λ max 529 (6,230), 493 (11,815), 478 (11,690), 287 (6,835), 248 (22,820), and 233 (35,615) nm; nmr of free base δ 0.93 (t, J=6 Hz, 3H, 19—CH$_3$), 1.38 (d, J=6 Hz, 3H, 5'—CH$_3$), 3.7 (broad s, 2H, NHCH$_2$C$_6$H$_5$), 4.03 (s, 3H, Ar—OCH$_3$), 5.17 (m, 3H, 7—H and 14—H$_2$), 5.48 (bs, 1H, 1'—H), 7.22 (s, 5H, NHCH$_2$C$_6$ $_5$), 7.28–8.00 (m, 3H, Ar—H).

Analysis: Calculated for C$_{39}$H$_{43}$NO$_{12}$.HCl.H$_2$O: C, 60.65; H, 6.02; Cl, 4.59; N, 1.81; Found: C, 60.47; H, 6.21; Cl, 4.38; N, 1.76.

Method B

Adriamycin-14-valerate HCl (300 mg, 0.45 mmol) was stirred at room temperature in dimethylformamide (6 ml) with triethylamine (0.1 ml) and α-iodotoluene (0.1 ml) for 10 min. Triethylamine (0.05 ml) and α-iodotoluene (0.05 ml) were added in succession at 10 min. intervals, until there was no longer evidence of starting material (hplc). The solvents were removed on the rotary evaporator under high vacuum. The residue was chromatoraphed on Biosil A silicic acid (15 g). CHCl$_3$—MeOH (1%) eluted pure N-benzyladriamycin-14-valerate. This, combined with more material obtained by preparative tlc of mixed fractions, yielded 205 mg of product, the hydrochloride salt of which was prepared as usual, (210 mg, 62%). Material thus obtained was identical in properties with that obtained by Method A.

EXAMPLE 2

N,N-Di(n-propyl)adriamycin-14-valerate

Adriamycin-14-valerate HCl (300 mg, 0.45 mmol) in acetonitrile water (3:1, 19 ml) was stirred at room temperature with propionaldehyde (0.15 ml) for 30 min. NaCNBH$_3$ (80 mg, 1.3 mmol) was added and stirring was continued at room temperature for 4 hr. The product, worked up as described in Example 1, was chromatographed on silica gel (16 g). CHCl$_3$—MeOH (0.8%) eluted pure N,N-Di(n propyl)-adriamycin-14-valerate (158 mg, 47%), the hydrochloride salt of which was homogeneous on tlc (CHCl$_3$—MeOH, 9:1, R$_f$ 0.68) and hplc (same as in Example 1, except isocratic separation 65% CH$_3$CN, 35% pH 4.0 buffer, r.t.=3.15 min); uv-vis λ max 528 (6,650), 493 (11,795), 477 (11,960), 285 (9,320) 250 (22,805) and 232 (30,320) nm; nmr of free base δ 0.80 (t, J=6.0 Hz, 6H, N[(CH$_2$)$_2$CH$_3$]$_2$), 0.95 (t, J=6 Hz, 3H, 19—CH$_3$), 1.35 (d, J=6 Hz, 5'—CH$_3$), 4.05 (s, 3H, ArOCH$_3$), 5.23 (m, 3H, 7—H, 14—H$_2$), 5.52 (bs, 1H, 1'—H), 7.33–8.01 (m, 3H, Ar—H), 13.07 (s, 1H, phenolic OH), 13.92 (s, 1H, phenolic OH).

Analysis: Calculated for C$_{38}$H$_{49}$NO$_{12}$. 1.1HCl.1.5H$_2$O: C, 58.58; H, 6.88; Cl, 5.00; N, 1.79; Found: C, 58.50; H, 7.22; Cl, 5.19; N, 1.74.

The corresponding N mono(n-propyl) adriamycin-14-valerate could be eluted from the silica gel with CHCl$_3$—MeOH (3%) in a yield of 25%.

EXAMPLE 3

N,N-Di(n-butyl)adriamycin-14-valerate

To a stirred solution of adriamycin-14-valerate HCl (300 mg, 0.45 mmol) in CH$_3$CN:H$_2$O (3:1, 15 ml) was added butyraldehyde (0.3 ml), and the mixture was stirred for 30 min. NaCNBH$_3$ (80 mg, 1.3 mmol) was added and stirring was continued at room temperature for 24 hr. The residue obtained after the work-up described in Example 1 was chromatographed on silica gel (20 g). CHCl$_3$—MeOH (0.2%) eluted pure N,N-Di-(n-butyl)adriamycin-14-valerate the hydrochloride salt (195 mg. 56%) was homogeneous on tlc (CHCl$_3$—MeOH, 9:1, R$_f$ 0.72) and hplc (same as in Example 1, except isocratic separation 65% CH$_3$CN, 35% pH 4.0 buffer, r.t.=4.34 min.); uv-vis λ max 528 (7,185), 494 (12,470), 477 (12,515), 287 (9,155), 250 (23,200) and 232 (30,195) nm; nmr of free base 0.90 (t, unresolved, 9H, 19—CH$_3$, and N[CH$_2$)$_3$,CH$_3$]$_2$), 1.35 (d, on top of methylene signal, 5'—CH$_3$), 4.02 (s, 3H, Ar—OCH$_3$), 4.53 (s, disappearing on D$_2$O exchange, 9—OH), 5.18 (bs, 3H, 7—H and 14—H$_2$), 5.53 (m, 1H, 1'—H), 7.34–8.00 (m, 3H, Ar—H), 13.08 (s, 1H, phenolic OH), 13.92 (s, 1H, phenolic OH).

Analysis: Calculated for C$_{40}$H$_{53}$NO$_{12}$.HCl.2H$_2$O: C, 59.13; H, 7.21; Cl, 4.36; N, 1.72; Found: C, 59.32; H, 7.22; Cl, 4.17; N, 2.02.

The toxicity and therapeutic effectiveness of the new compounds and active agents of the present invention are shown by in vitro assays and by in vivo evaluations in mice. The in vitro assays measure the growth inhibiting activity of the materials against the CCRF-CEM cell line in culture. The cell line was derived from the peripheral blood of a child with lymphoblastic leukemia as described by Foley et al., Cancer, Volume 18, page 522 et seq. (1965), and the assays were carried out by the procedure of Foley and Lazarus, Biochem. Pharmacol., Vol. 16, pages 659 et seq. (1967), the compounds being dissolved in dimethyl sulfoxide and diluted into cell culture media to give a final dimethyl sulfoxide concentration of 1%, the results being reported in terms of the dose in micromoles per liter required to inhibit growth of the cultures by 50% relative to control cultures to which no drug had been added (ID$_{50}$).

The results were as follows:

| Product | ID$_{50}$ μM[1] |
|---|---|
| Example 1 | 1.0 |
| Example 2 | 1.9 |
| Example 3 | 2.1 |

[1]Concentration required to inhibit growth of cultures by 50% relative to untreated controls; 48 hours continuous drug exposure.

In contrast, the results for corresponding compounds having different N-substitution were as follows: dimethyl, 0.02; diethyl, 0.30; mono-n-propyl, 0.17; di-n-hexyl, 2.5; dibenzyl, >5.0.

While the foregoing in vitro test results do not correlate with in vivo antitumor activity, they are useful as an index of toxicity and for an indication of initial dose ranges to be used in in vivo antitumor assays.

The in vivo evaluations were made by preparing a 0.01 to 0.4% by weight solution of the active agent in an aqueous solution of polyethoxylated castor oil (10% by volume) and ethanol (10% by volume) as a carrier and injecting the dosage intraperitoneally. The evaluations were made of the antitumor activity against the murine P 388 and L1210 leukemias in B6D2F1 male mice essentially according to standard National Cancer Institute protocols as set forth by Geran et al., Cancer Chemotherap. Rep., Part 3, Volume 3, pages 1 et seq. (1972), except that a qd 1–4 schedule was used in place of qd 1–9 based upon the greater efficacy of this schedule modification for various adriamycin analogues and derivatives.

The results against murine P 388 leukemia were as follows:

| Product | Optimal Dose[1] mg/kg qd 1-4 | % ILS[2] | LTS (day)[3] |
|---|---|---|---|
| Example 1 | 10.0 | > +770 | 7/7 (88) |
| Example 2 | 20.0 | > +570 | 4/7 (67) |
| Example 3 | 30.0 | > +770 | 4/7 (88) |

[1]Highest non-toxic dose.
[2]Percent median increase in life span relative to untreated controls.
[3]Tumor free long term survivors (day of sacrifice).

In contrast, the results against P 388 leukemia were as follows for corresponding compounds having the same N-substitution but lacking the A substituent as in Examples 1, 2 and 3, having instead in its place OH.

| Product | Optimal Dose[1] mg/kg qd 1-4 | % ILS[2] | LTS (day)[3] |
|---|---|---|---|
| Mono-N—benzyl | 5.0 | +180 | 1/7 (77) |
| Di-n-propyl | 20.0 | +260 | 2/7 (67) |
| Di-n-butyl | 25.0 | +220 | 1/7 (77) |

In further contrast, the results against P 388 leukemia were as follows for corresponding compounds having $R_3$ equal to valerate but different N-substitution:

| Product | Optimal Dose[1] mg/kg qd 1-4 | % ILS[2] | LTS (day)[3] |
|---|---|---|---|
| Diethyl | 8.0 | +90 | 0 |
| Mono-n-propyl | 15.0 | +190 | 2/7 (67) |
| Di-n-hexyl | 40.0 | +63 | 0 |
| Dibenzyl | 20.0 | +145 | 1/7 (100) |

The results against murine L1210 leukemia, as compared with the parent adriamycin, were as follows:

| Product | Optimal Dose[1] mg/kg qd 1-4 | % ILS[2] | LTS (day)[3] |
|---|---|---|---|
| Example 1 | 12.5 | > +350 | 5/7 (42) |
| Example 2 | 20.0 | > +350 | 4/7 (42) |
| Example 3 | 25.0 | > +350 | 5/7 (42) |
| Adriamycin | 3.0 | +90 | 0/7[4] |

[4]All animals dead by day 22.

What is claimed is:
1. Compounds having the following structure

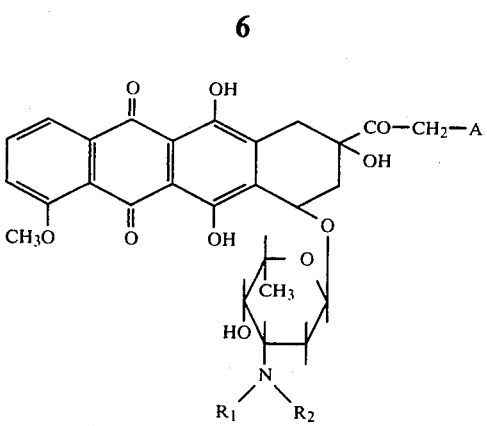

in which A is alkanoate having from 4 to 10 carbon atoms, hemiadipate, or hemiglutarate, and in which $R_1$ and $R_2$ are n-propyl or n-butyl, or in which $R_1$ is hydrogen, n-propyl or n-butyl and $R_2$ is benzyl, and their corresponding non-toxic pharmacologically acceptable acid salts.

2. Compounds as claimed in claim 1 in which A is valerate.

3. A compound as claimed in claim 2 in which $R_1$ is hydrogen and $R_2$ is benzyl.

4. A compound as claimed in claim 2 in which $R_1$ and $R_2$ are both n-propyl.

5. A compound as claimed in claim 2 in which $R_1$ and $R_2$ are both n-butyl.

6. A therapeutic composition exhibiting antitumor activity consisting essentially of a pharmacologically acceptable non-toxic carrier and an effective amount of a compound as claimed in claim 1.

7. A therapeutic composition exhibiting antitumor activity consisting essentially of a pharmacologically acceptable non-toxic carrier and an effective amount of a compound as claimed in claim 2.

8. A therapeutic composition exhibiting antitumor activity consisting essentially of a pharmacologically acceptable non-toxic carrier and an effective amount of a compound as claimed in claim 3.

9. A therapeutic composition exhibiting antitumor activity consisting essentially of a pharmacologically acceptable non-toxic carrier and an effective amount of a compound as claimed in claim 4.

10. A therapeutic composition exhibiting antitumor activity consisting essentially of a pharmacologically acceptable non-toxic carrier and an effective amount of a compound as claimed in claim 5.

* * * * *